United States Patent [19]

Sundberg et al.

[11] 3,994,966
[45] Nov. 30, 1976

[54] CHELATING AGENTS

[75] Inventors: Michael W. Sundberg, Stanford; Claude F. Meares, Davis, both of Calif.; Lucius Werthemann, Kaenelrain, Switzerland

[73] Assignee: The Board of Trustees of the Leland Stanford Junior University, Stanford, Calif.

[22] Filed: Sept. 28, 1972

[21] Appl. No.: 293,083

[52] U.S. Cl. .................. 260/518 R; 260/507 R; 260/562 R; 260/570.5 P; 250/303; 250/493
[51] Int. Cl.² .............. C07C 101/42; C07C 101/48; C07C 143/52
[58] Field of Search .................... 260/507 R, 518 R

[56] References Cited
UNITED STATES PATENTS

| | | | |
|---|---|---|---|
| 2,763,680 | 9/1956 | Sallmann | 260/507 R |
| 3,293,176 | 12/1966 | White | 260/507 R |

OTHER PUBLICATIONS

Tsirul'Nikova et al., Chemical Abstract, vol. 75, p. 334, (1971).
Okaku, Chem. Abstracts, 68, 12641b, (1968).
Cram et al., "Organic Chemistry", 2nd edition, pp. 17–18, (1964).

Primary Examiner—James O. Thomas, Jr.
Assistant Examiner—Nicky Chan

[57] ABSTRACT

Chelating agents having in addition to their metal sequestering groups a functional group capable of reacting with bio-organic molecules are disclosed, in particular, substituted ethylenedinitrilotetraacetic acids such as 1-p-nitrophenylethylenedinitrilotetraacetic acid, 1-p-aminophenylethylenedinitrilotetraacetic acid and their derivatives are disclosed. These compounds are effective chelating agents and in addition are useful in the perturbed angular correlation method of studying molecular behavior.

2 Claims, No Drawings

CHELATING AGENTS

The invention described herein was made in the course of work under a grant or award from the Department of Health, Education and Welfare.

BACKGROUND AND SUMMARY OF THE INVENTION

Ethylenedinitrilotetraacetic acid is a well-known and widely used chelating agent. It does not appear that there have been compounds available which result from the substitution of a functional group capable of reacting with a biological macromolecule for one or more of the hydrogen atoms of the ethylene group of ethylenedinitrilotetraacetic acid. Compounds having such substituents would vary in chelating activity of the molecule and would open the way to ethylenedinitrilotetraacetic acid-metal chelates having varied chemical and physical properties and extending utility.

U.S. Pat. No. 3,665,192 describes a method for studying the behavior of biological macromolecules by attaching a radioactive label to the macromolecule and then observing the extent of perturbation of the angular correlation of the radiation emitted by the radioactive label. The method is sophisticated but it opens the way to more definitive study of the structures of biological macromolecules.

In order to make efficient use of this technique, it is necessary to have available radioactive labels which will attach and adhere to the macromolecules to be studied. An effective label would be a radioactive metal ion bound by a powerful chelating agent which in addition to its metal sequestering groups contains an active functional group which can bond the metal chelate to a biological macromolecule. Such effective labels are produced pursuant to this invention by (1) producing N,N'-diacetyl 1-phenylethylenediamine and (2) introducing a functional group into its benzene ring, for example by subjecting it to nitration, nitration and reduction, sulfonation or acylation, (3) hydrolyzing the reaction products and (4) reacting each hydrolysis product with Bromoacetic acid. In this manner ethylene dinitrilotetraacetic acids of the formula

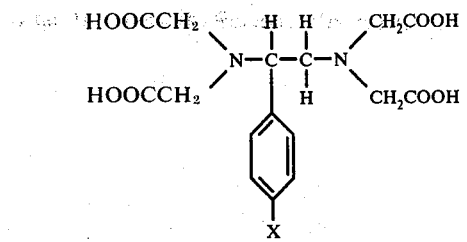

in which X is a functional group, are produced. Groups such as $NO_2$, $NH_2$, $SO_3H$,

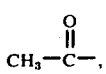

OH, COOH provide the desired functionality.

DETAILED DESCRIPTION OF THE INVENTION

EXAMPLE I 1-p-nitrophenylethelyenedinitrilotetraacetic acid is produced by (a) preparing N,N'-diacetyl 1-phenylethylenediamine, (b) nitrating it, (c) hydrolyzing the nitration reaction product and reacting the hydrolysate with bromoacetic acid as follows:

Step I: Preparation of N,N'-diacetyl 1-phenylethylenediamine

1-Phenylglycinonitrile was synethsized from benzaldehyde by the method of Steiger (Organic Synthesis Col. Vol III, 84 [1965]) except that the nitrile was isolated by extraction with ethyl acetate, back extracted with water, dried with anhydrous magnesium sulfate and precipitated as its salt with dry hydrogen chloride.

Step II: Hydrogenation

A mixture of 33 gm of 1-phenylglycinonitrile-HCl, 24 gm of sodium acetate, 250 ml of acetic anhydride, and approximately 2–3 gm of active Raney nickel was heated to 45°–55° and shaken under an initial hydrogen pressure of 40 p.s.i. until hydrogen uptake ceased (2–4 hr.). The mixture was then filtered and the solvent removed in vacuo. The resulting gummy solid was recrystalized from ethyl acetate-hexane to give 28.8 gm (67%) of white needles, m.p. 155°–156°.

Step III: Nitration of N,N'-diacetyl 1-phenylethylenediamine

Three grams of N,N'-diacetyl 1-phenylethylenediamine was added slowly to 10 ml of 90% nitric acid at −40°. After stirring for 3 hr. the solution was poured on ice and neutralized with sodium bicarbonate. The resulting mixture was extracted with ethyl acetate. The ethyl acetate was dried with anhydrous magnesium sulfate, and removed in vacuo. N,N'-Diacetyl 1-p-nitrophenylethylenediamine was recrystalized from acetone-hexane to give 2.2 gm (61%) of white needles, m.p. 179°–180°.

Anal: Calc'd for $C_{12}H_{15}N_3O_4$: C, 54.33; H, 5.70; N, 15.84%. Found: C, 54.59; H, 5.73; N, 16.05%.

Step IV: Hydrolysis of N,N'-diacetyl 1-p-nitrophenylethylenediamine

A solution of 2.65 gm of N,N'-diacetyl 1-p-nitrophenylethylenediamine in 12 ml acetic acid, 2 ml water, and 18 ml conc. hydrochloric acid was heated at reflux for 20 hr., cooled in ice, filtered, made strongly basic, and extracted with methylene chloride. The organic phase was dried with anhydrous magnesium sulfate and dry hydrogen chloride was introduced. The resulting solid was combined with the original precipitate (if any) and washed with methanol. The yield was 1.68 gm (66%) of 1-p-nitrophenylethylenediamine-2HCl, m.p. 220°–241° (decomp.).

Anal: Calc'd for $C_8H_{11}N_3O_2$-2HCl: C, 37.82; H, 5.15; N, 16.54%. Found: C, 37.52; H, 5.15; N, 16.69%.

Step V: Preparation of 1-p-nitrophenylethylenedinitrilotetraacetic acid

A solution of .610 gm of 1-p-nitrophenylethylenediamine-2HCl and 1.6 gm of bromoacetic acid in 10 ml of water was heated to 40°-5-°, and 7 M potassium hydroxide was added to maintain the pH of the solution between 10 and 11. When the reaction was complete (8 hr.) the solution was acidified with conc. hydrochloric acid and placed in the cold. Within a few days 411 mg (40%) of a white solid separated. A portion was purified on an anion exchange column (Bio-Rad AG 1-X8, exchanged to the formate form). The purified material melted at 171°–174° (decomp.).

Anal: Calc'd for $C_{16}H_{19}N_3O_{10} \cdot H_2O$: C, 44.54; H, 4.90; N, 9.74%. Found: C, 44.59% H, 4.83; N, 9.67%.

EXAMPLE II

Amino-phenylethylenedinitrilotetraacetic acid was produced by reducing 1-p-nitrophenylethylenedinitrilotetraacetic acid as follows:

30 mg of nitrophenylethylenedinitrilotetraacetic acid is dissolved in 1.0 ml of 0.6 N NaOH and 42 mg of $Na_2S_2O_4$ is added. After brief stirring the solution is heated on a steam bath for ½ hr. Reduction of the nitro group to an amine group was confirmed by examination of the NMR spectrum of the residue after evaporation.

EXAMPLE III

N,N'-diacetyl 1-phenylethylenediamine prepared as in Example I was acetylated as follows:

1.0 gm of N,N'-diacetylphenylethylenediamine is mixed with 6 ml of $CCl_4$ at 50° and added to it are 3 ml of acetyl bromide and 4 gm of $AlCl_3$. The mixture was heated on an oil bath at 70° for 1 hr. The resulting brown material was eluted from a silica gel column with $CHCl_3$ and then 10% methanol-$CHCl_3$. The middle portion of the eluate crystallized. NMR examination of the crystals confirmed the presence of the

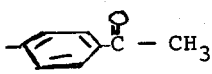

structure.

The crystalline solid is then treated as in steps IV and V of Example I to produce

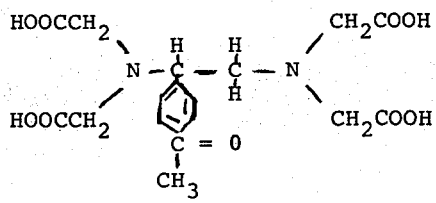

EXAMPLE IV

N,N' diacetyl 1-phenylethylenediamine produced as in Example I is sulfonated as follows:

Add 0.04 mole N,N'-diacetylphenylethylenediamine to 7.5 gm of 20% oleum ($SO_3$ in $H_2SO_4$) slowly to keep temperature from rising sharply. After complete addition gradually raise temperature to 175° F over a two hour period. Then cool and neutralize with 10% NaOH, adjust pH to 7 and collect solid. The solids then treated as in steps IV and V of Example I to produce

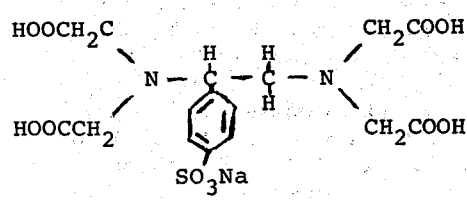

We claim:
1. Ethylene dinitrilotetraacetic acids having the formula

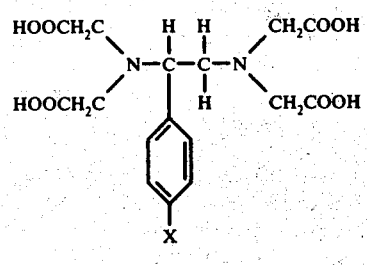

wherein X is $NO_2$, $SO_3H$, $NH_2$ or

2. 1-p-nitrophenylethylenedinitrilotetraacetic acid.

* * * * *